United States Patent [19]
Ball

[11] Patent Number: 5,866,426
[45] Date of Patent: Feb. 2, 1999

[54] DEVICE AND METHOD FOR DETERMINING LIQUID-PROBE CONTACT

[75] Inventor: Stuart R. Ball, Yukon, Okla.

[73] Assignee: Akzo Nobel N.V., Arnhem, Netherlands

[21] Appl. No.: 768,742

[22] Filed: Dec. 17, 1996

[51] Int. Cl.$^6$ .............................. G01N 35/10; G01N 1/10
[52] U.S. Cl. .............................. 436/54; 436/180; 422/62; 422/68.1; 422/106; 422/108; 73/864.24; 73/304 C; 340/620
[58] Field of Search .............................. 340/620; 422/62, 422/63, 68.1, 106, 105, 107, 108; 436/174, 54, 180; 73/863.02, 864.24, 304 C

[56] References Cited

U.S. PATENT DOCUMENTS

| | | |
|---|---|---|
| 4,112,318 | 9/1978 | Hamelink . |
| 4,173,893 | 11/1979 | Hedrick . |
| 4,332,167 | 6/1982 | Sun et al. . |
| 4,380,091 | 4/1983 | Lively . |
| 4,509,044 | 4/1985 | Yachida . |
| 4,540,981 | 9/1985 | Lapetina et al. . |
| 4,733,560 | 3/1988 | Dam . |
| 4,736,638 | 4/1988 | Okawa et al. . |
| 4,768,377 | 9/1988 | Habelmann et al. . |
| 4,789,946 | 12/1988 | Sinz . |
| 4,875,497 | 10/1989 | Worthington . |
| 4,912,976 | 4/1990 | Labriola, II . |
| 5,049,826 | 9/1991 | Sasao . |
| 5,178,019 | 1/1993 | Keiter . |
| 5,220,514 | 6/1993 | John . |
| 5,236,666 | 8/1993 | Hulette et al. . |
| 5,275,951 | 1/1994 | Chow et al. . |
| 5,354,537 | 10/1994 | Moreno . |
| 5,365,783 | 11/1994 | Zweifel . |
| 5,493,922 | 2/1996 | Ramey et al. ........................ 73/863.02 |

*Primary Examiner*—E. Leigh McKane
*Attorney, Agent, or Firm*—Gregory R. Muir

[57] ABSTRACT

A sensor detects when a probe contacts liquid in a container due to a change in frequency of a probe oscillator. The sensor can have its output compared to a reference level to determine the presence or absence of liquid wherein the reference level is changed to follow the output of the detector. In one embodiment, it can be determined that liquid has been contacted when a count has been reached several times in a row (the count being a function of the probe output and changeable). In another embodiment of the invention, it can be determined that liquid has been contacted when a count has been reached within a certain threshold several times in a row, while still having the reference count change to follow the probe output (regardless of the threshold). A digital counter can be provided to determine the frequency of the probe oscillator. A reference counter can also be provided to tune the count (frequency) from the probe oscillator counter to thereby compensate for drift. And, the adjustable detection threshold permits control of the sensitivity by changing the parameters of the circuit.

23 Claims, 5 Drawing Sheets

DEVICE AND METHOD FOR DETERMINING LIQUID-PROBE CONTACT

BACKGROUND OF THE INVENTION

1. Field of the Invention

The present invention relates to a method and apparatus for detecting a surface of a liquid in a container, and to a method and apparatus for use in an automated blood/plasma sampling system for detecting a surface of a liquid in a container and for controlling a position of a probe with respect to the surface of the liquid. More particularly, the present invention relates to a method and apparatus for maintaining accuracy of the liquid detection over a period of time.

An example of an automated blood/plasma sampling system for which the present invention is applicable is disclosed, for example, in U.S. Pat. No. 5,236,666 to Hulette et al. The subject matter of this patent to Hulette et al. is incorporated herein by reference. An example of a piercing and sampling probe is disclosed in U.S. Pat. No. 5,354,537 to Moreno. The subject matter of the patent to Moreno is incorporated herein by reference. Another example of a sampling probe is disclosed in U.S. Pat. No. 5,178,019, issued Jan. 12, 1993, to Keiter. The subject matter of the patent to Keiter is incorporated by reference herein. An example of a liquid level sensing probe and control circuit is disclosed in U.S. Pat. No. 5,493,922, to Ramey et al. The subject matter of the patents to Hulette et al., to Moreno, to Ramey et al. and to Keiter are each assigned to the same assignee as the present application.

Automated sample handling systems are known which automatically dispense fluid samples, such as blood plasma and reagents, into a reaction well of a cuvette. Such instruments are useful in the field of biochemical analysis for measuring blood clotting times and for automatically carrying out chemical assays. An automated sample handling system for carrying out blood and plasma bioassays is described in U.S. Pat. No. 5,236,666, to Hulette et al.

In this particular system, fluid samples, such as blood or plasma, are stored in containers, such as test tubes, which are vacuum sealed by way of a rubber septum that must be pierced in order to withdraw a measured amount of the sample for testing purposes. U.S. Pat. No. 5,354,537 to Moreno, discloses an example of a piercing and sampling probe suitable for piercing and sampling a measured amount of liquid.

The Hulette et al. system also includes a temperature controlled housing provided for storing fluid samples and reagents at a relatively cool temperature for preventing degradation of the samples and reagents prior to sample analysis. The temperature controlled housing typically maintains the fluid samples and reagents at a temperature of 10° C. The actual analyses are generally carried out at 37° C. (98.6° F.), standard human body temperature. Accordingly, it is necessary to heat the fluid sample and reagents to 37° C. prior to analysis. U.S. Pat. No. 5,178,019, to Keiter, discloses a sample probe device useful for heating fluid samples and reagents prior to analysis.

The piercing and sampling probes in the Hulette et al. system are raised and lowered in operation by a robotic arm which maneuvers a probe between reagent containers and a reaction cuvette for automatically aspirating and dispensing reagents. The surface of a liquid, whether a sample or reagent, is detected for accurately controlling movement of the probe. Basically, the surface of the liquid is detected by detecting a change in capacitance of the probe with respect to the chassis of the automated blood/plasma sampling system.

DESCRIPTION OF THE RELATED ART

In U.S. Pat. No. 5,493,922 to Ramey et al., a method and apparatus are disclosed which are for a liquid level sensor control circuit of a bioassay apparatus for controlling a position of a sampling probe with respect to a surface of a liquid in a container. The apparatus includes a sampling probe, an oscillator circuit coupled to the sampling probe for producing a first output signal having a constant frequency, a comparator coupled to the oscillator circuit for comparing the amplitude of the first output signal to a first reference amplitude and for producing a change signal when the amplitude of the first output signal changes with respect to the reference amplitude, and a controller responsive to the change signal for controlling the position of the sampling probe with respect to the surface of the liquid. In one embodiment in Ramey et al., a filter is provided in communication with the oscillator circuit to servo the oscillator output signal to a fixed level by controlling the amplitude of the first output signal. The amplitude of the first output signal changes in response to a capacitance change when the probe touches the surface of the liquid.

However, when the temperature of a probe changes, or foam or droplets of liquid adhere to the probe, the related art systems may output a faulty indication of a liquid level. Because temperature, foam, liquid droplets and other external factors besides the liquid body may also influence the oscillation of the probe, these factors may also influence the probe systems to falsely indicate the presence of liquid.

SUMMARY OF THE INVENTION

The present invention accurately senses a surface of a liquid when a probe, such as a piercing or sampling probe, for a bioassay apparatus touches the surface of the liquid. Over a period of time, the accuracy of the liquid level sensing system is maintained.

The above and other objects of the invention are accomplished by the provision of a liquid level sensor for controlling a position of a sampling probe with respect to a surface of a liquid in a container, including a sampling probe for touching the surface of the liquid in the container and a probe oscillator electrically connected to the (conductive) probe. The probe is moved mechanically to contact the liquid in the container. The container rests on, or is in close proximity to, a grounded conductor. When the probe contacts the liquid, the liquid with the grounded conductor, forms a capacitor that is in parallel with a frequency-determining capacitor on the probe oscillator. Contact of the probe with the liquid therefore lowers the frequency of the probe oscillator.

In the present invention, the probe/liquid detector can have its output compared to a reference level to determine the presence or absence of liquid wherein the reference level is changed to follow the output of the detector. In one embodiment of the invention, it can be determined that liquid has been contacted when a count has been reached several times in a row (the count being a function of the probe output and changeable). In another embodiment of the invention, it can be determined that liquid has been contacted when a count has been reached within a certain threshold several times in a row, while still having the reference count change to follow the probe output (regardless of the threshold). A digital counter can be provided to determine the frequency of the probe oscillator. A reference counter can also be provided to tune the count (frequency) from the probe oscillator counter to thereby compensate for drift. And, the adjustable detection threshold permits control of the sensitivity by changing the parameters of the circuit.

BRIEF DESCRIPTION OF THE DRAWINGS

A preferred embodiment of the invention will be described in conjunction with the accompanying drawings.

DETAILED DESCRIPTION OF THE INVENTION

Figure 1:
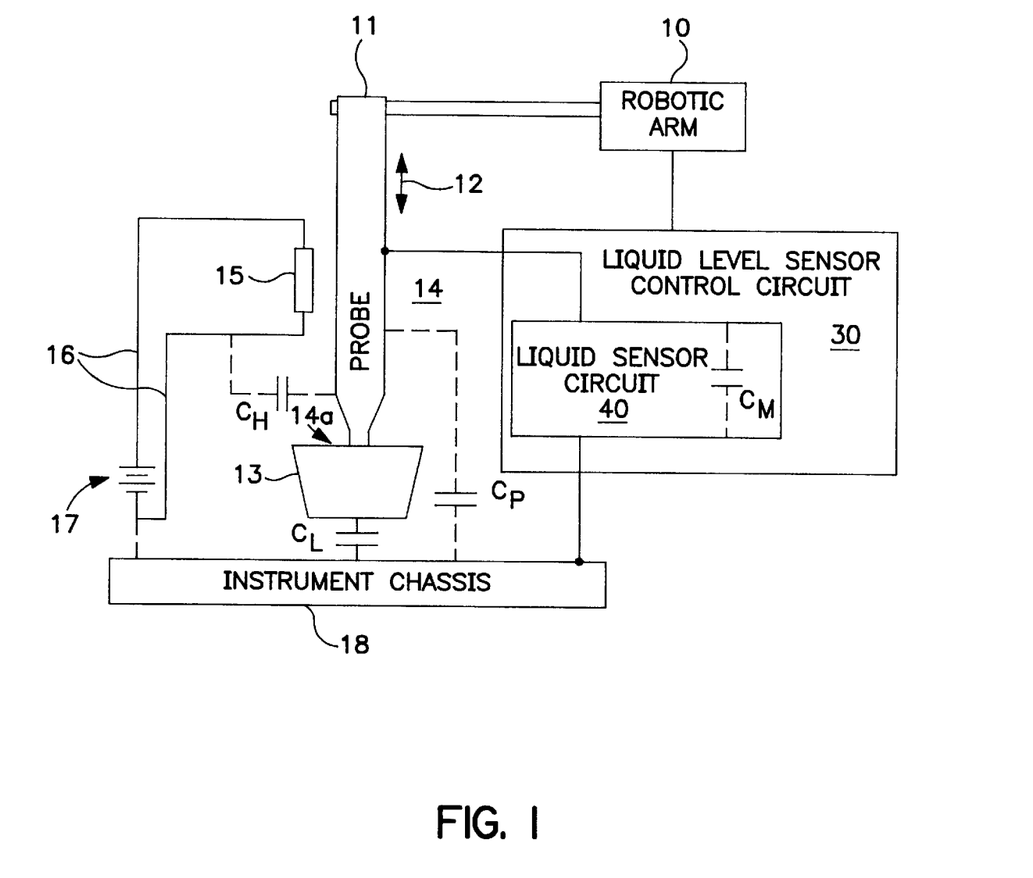
FIG. 1 is a schematic block diagram of an embodiment of a probe and a liquid sensor control circuit according to the present invention.

FIG. 1 shows a schematic block diagram of an embodiment of a probe for an automated blood/plasma sampling system and its relation to a liquid sensor circuit and control circuit according to the present invention. Robotic arm 10 maneuvers probe 11 between reagent containers, such as reservoir 13, to a reaction cuvette (not shown) for automatically aspirating and dispensing reagents as described, for example, in U.S. patent application Ser. No. 07/443,951, to Hulette et al. Robotic arm 10 raises and lowers probe 11 along the directions indicated by arrow 12 for taking a measured volume of liquid from liquid reservoir 13 or dispensing it to a reaction cuvette. Generally, probe 11 includes a metallic tube 14 having a narrow tip 14a for dipping into reservoir 13 and aspirating a measured amount of reagent. Probe 11 may also be adapted for piercing a container sealed by a rubber septum to aspirate a measured volume of liquid from the container by including a pointed tip.

As previously mentioned, it is desirable in certain applications to heat the reagent within probe 11 while the probe is moved by robotic arm 10 toward a cuvette where the reagent is dispensed. In these applications, probe 11 is provided with an optional heater 15. Heater 15 preferably includes a coiled nichrome wire wrapped around tube 14 and electrically connected by wires 16 to a power supply 17 which shares a common ground with chassis 18. Power supply 17 can either be a DC or AC power supply depending on the requirements of a particular application. In order to aspirate a measured amount of reagent from reservoir 13, it is necessary to detect when probe 11 contacts the surface of the reagent. As previously discussed, this is typically accomplished with the use of a capacitance measuring device for detecting a change in the capacitance of tube 14 with respect to the ground plane formed by chassis 18 when tube 14 contacts the reagent on reservoir 13. Tube 14 presents a first capacitance $C_P$ with respect to chassis 18. When optional heater 15 is provided, heater 15 has a common ground with instrument chassis 18 and, therefore, is capacitively a part of chassis 18. Thus, optional heater 15 presents a second capacitance $C_H$ with respect to tube 14. Liquid reservoir 13 presents an additional capacitance $C_L$ between probe 11 and instrument chassis 18. Thus, before probe 11 touches the surface of the liquid, the total capacitance $C_{T1}$ measured by the capacitance measuring device is $C_{T1}=C_P+C_H.$ If an optional heater is not provided, $C_H$ equals zero and the total capacitance $C_{T1}$ is $C_P$. After probe 11 touches the surface of the liquid, the total capacitance $C_{T2}$ measured by the capacitance measuring device is $C_{T2}=C_P+C_L+C_H.$ Detection of the additional capacitance $C_L$ be a capacitance measuring device indicates when probe 11 contacts the liquid surface in container 13. However, the presence of capacitance $C_H$ caused by an optional heater can be sufficiently large to limit the ability of the capacitance measuring device to sense a change in $C_{T1}$ by $C_L$.

The liquid sensor circuit and liquid level sensor control circuit of the present invention reliably senses changes in capacitance between the probe and the system chassis even in the presence of an optional heater. In fact, the liquid level sensor system according to the present invention reliably senses the surface of, for example, liquid volumes less than 300 μl of saline in a plastic 3 ml reagent bottle, even while piercing a sealing septum.

Figure 2:
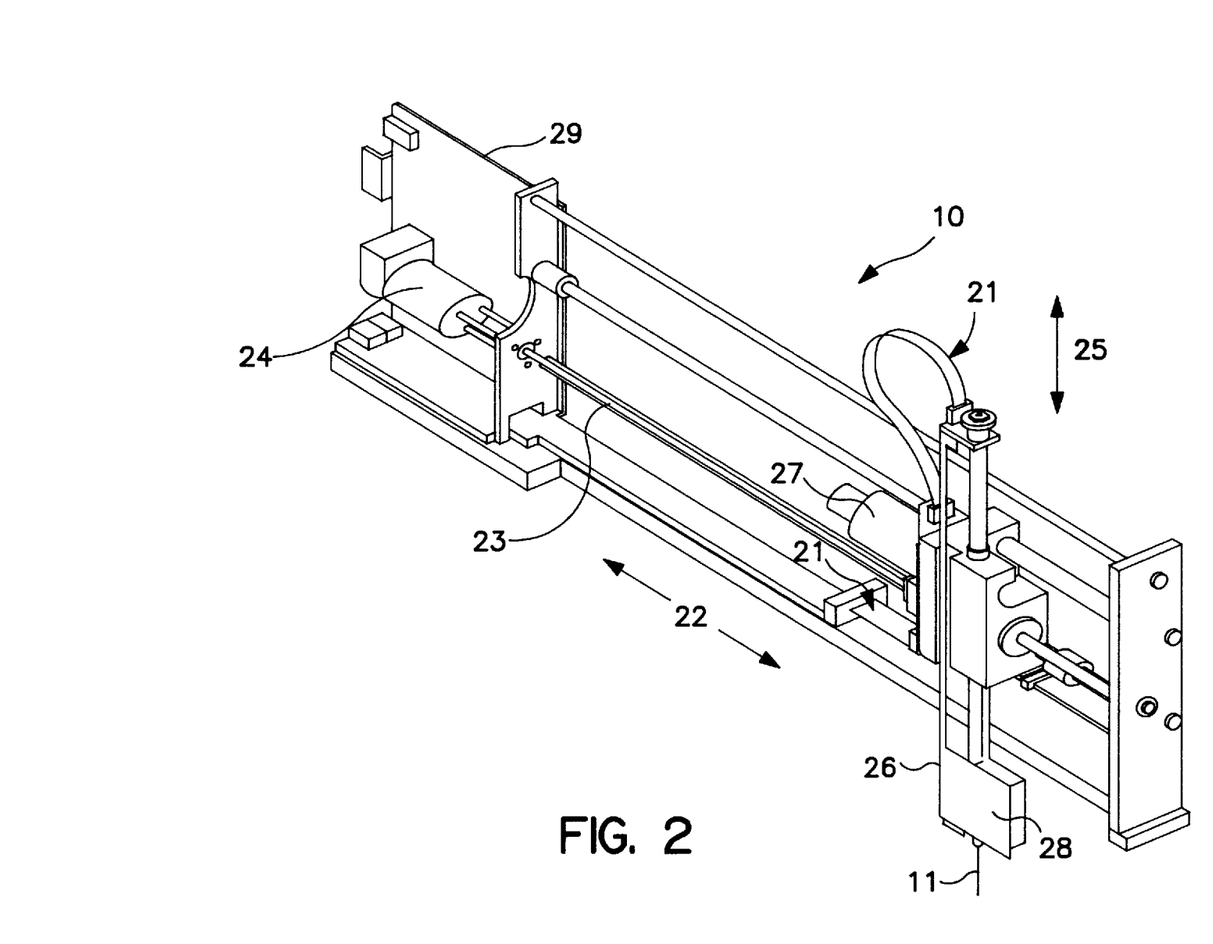
FIG. 2 is a perspective view of a robotic arm including a probe and a liquid level sensor control circuit according to the present invention.

FIG. 2 is a perspective view generally showing a preferred embodiment of robotic arm 10 including a probe 11 and a liquid level sensor control circuit according to the present invention. Probe 11 can be a sampling probe or a piercing and sampling probe for piercing rubber caps used to seal medical sample collection tubes, such as that disclosed in the previously mentioned application to Moreno. When probe 11 is a piercing sampling probe, it is preferably sharpened in accordance with the piercing probe disclosed in the previously mentioned patent to Moreno. Moreover, when probe 11 is a piercing sampling probe, it is adapted for detecting the surface of a liquid in a container when piercing the cap of the container. Probe 11 senses a liquid-air interface of a conductive liquid in container 13, such as blood or plasma, while probe 11 moves into container 13 for accurately positioning probe 11 with respect to the surface of the liquid.

Probe 11 is controllably moved into a horizontal axis 22 by lead screw 23 driven by horizontal lead screw motor 24. Vertical movement for raising and lowering probe 11 along axis 25 is provided by gear rack 26 driven by vertical motor 27 and a pinion assembly (not shown). Motors 24 and 27 are each selectively controlled by signals received from associated motor controllers, which are part of the liquid level sensor control circuit of the present invention. Motor controller 32, for example, is shown in the schematic block diagram of FIG. 3. Motor 27 provides sufficient torque for driving probe 11 through a septum of a sealed container when probe 11 is a piercing probe. Of course, the probe could be a vertically movable probe without any capabilities of horizontal movement, or the probe could be capable of moving vertically as well as in a plurality of directions in a horizontal plane. Also, if desired, the probe could be held stationary, with the sample container being moved upwardly in the direction of the probe.

Liquid level sensor control circuitry 30 is coupled to probe 11 for sensing a liquid-air interface. One portion of liquid level sensor control circuitry 30 can be located on a printed circuit board mounted at 29. Of course, the liquid level sensor control circuitry according to the present invention can be located together on a single printed circuit board.

Microcontroller 31 is a two-axis arm controller, that is, microcontroller 31 and the two motor controllers monitor and control the horizontal position of the rack assembly holding the probe 11 and the vertical position of probe 11 with respect to the surface of a liquid. Microcontroller 31 and motor controller 32 correlate the position of probe 11 with signals received from a liquid sensor circuit for determining the height of the liquid within the container. Flex cables 21 couple electrical signals between various portions of the control system according to the present invention. As previously mentioned, probe 11 can be fitted with a heating coil for preheating sampled fluids prior to dispensing into a reaction chamber.

Figure 3:
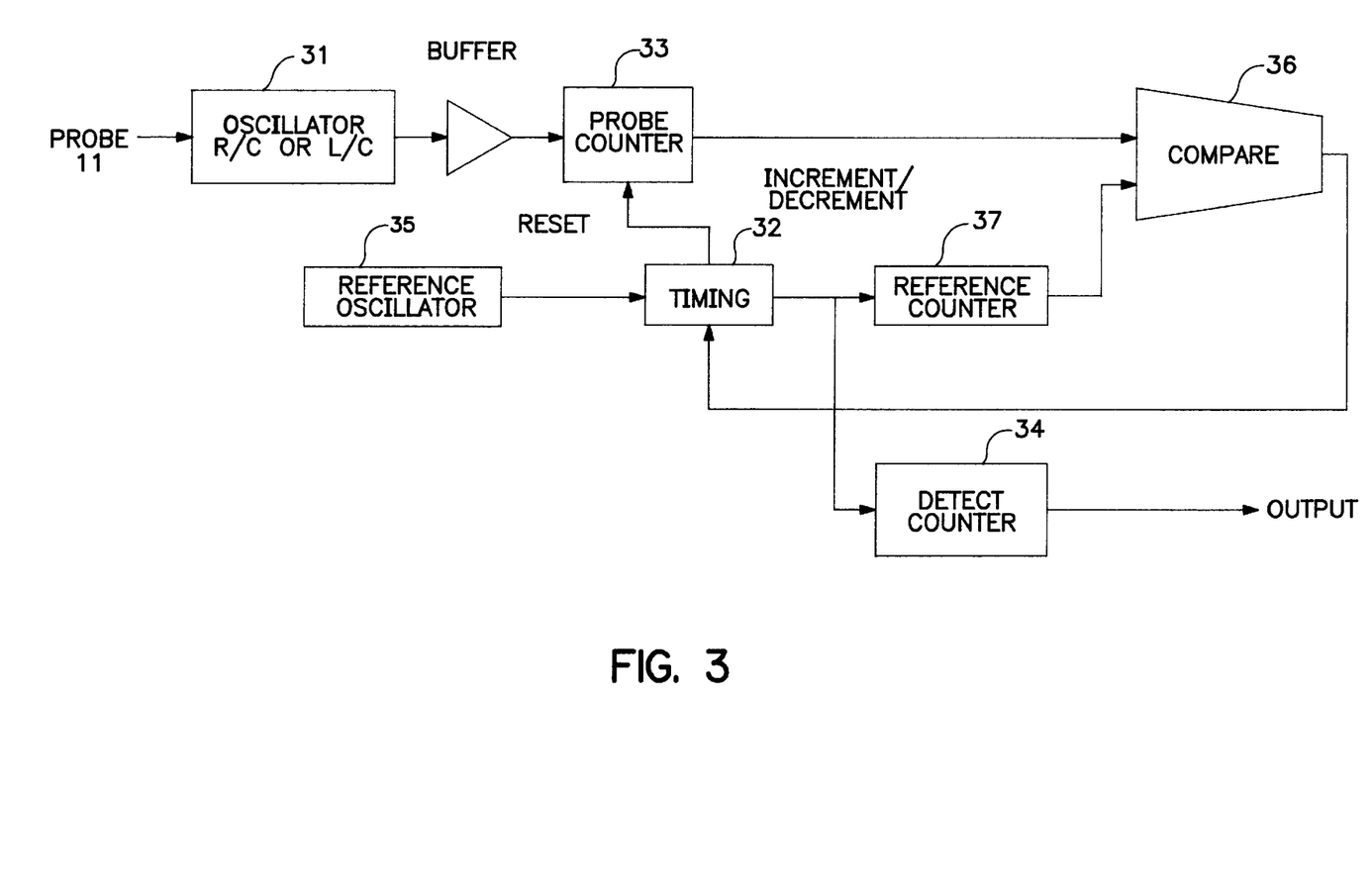
FIGS. 3, 4 and 5 are schematic block diagrams of different embodiments of a liquid level sensor control circuit.

FIG. 3 is a schematic block diagram of one embodiment of a liquid level sensor control circuit 30. Illustrated in FIG.

3 are probe 11 and R/C or L/C probe oscillator 31. Also shown are probe counter 33, reference counter 37 and detect counter 34. A comparator circuit 36, timing logic 32 and reference oscillator 35 are also shown.

In operation, probe 11 changes the tuning of the R/C or L/C probe oscillator 31 by shifting the frequency of the probe oscillator 31 down when probe 11 is in contact with liquid. Probe counter 33 counts the cycles of the frequency signal output by probe oscillator 31. Reference counter 37 stores an adjustable reference count. Comparator 36 compares the probe count stored in probe counter 33 with the reference count stored in reference counter 37.

At regular intervals, timing circuit 32 controls various operations of the probe counter 33, the reference counter 37 and the detect counter 34, explained below. In the preferred embodiment, the timing circuit 32 is programmable so that the regular interval may be adjusted for different sensing operations (for example, for sensing different types of liquid). Timing circuit 32 may constructed from any well known hardware or hardware/software combinations which perform the below described processes (such as a computer, a programmable integrated circuit). Reference oscillator 35 (such as a quartz oscillator) provides timing circuit 32 with a timing signal, such as a square wave clock signal. The timing logic typically consists of counters to divide the signal from the reference oscillator down to the reference interval period, and logic to generate and synchronize the signals needed to clock, load and clear the other components.

At the regular intervals, the reference counter 37 is adjusted by timing circuit 32 to follow the probe count in probe counter 33. If the contents of reference counter 37 are greater than the contents of probe counter 33, reference counter 37 is decremented. If the contents of reference counter 37 are less than the contents of probe counter 33, reference counter 37 is incremented. Then, timing circuit 32 clears the probe counter 33, resetting the probe count to zero.

Additionally, in response to the timing circuit 32, at each regular interval, the detect counter 34 counts the number of successive times the probe count in probe counter 33 is less than the reference count in reference counter 37. At each regular interval, when the comparison indicates the probe count to be greater than the reference count, the timing circuit 32 clears the detect counter 34, resetting its count. When a predetermined number of successive comparisons (sampled by timing circuit 32 at the regular interval) all indicate the probe count is less than the reference count, detect counter 34 outputs a liquid sensed signal, indicating that the probe 11 has contacted the liquid body.

In a more detailed embodiment, at every regular interval, the detect counter 34 increments or decrements with reference counter 37. Whenever the direction of the count of detect counter 34 changes (timing circuit 32 changes increment instruction to a decrement instruction, or a decrement instruction to an increment instruction), the detect counter 34 is reset, zeroing its count. When detect counter 34 decrements past a fixed count, it sets the liquid sensed output. In this manner, the circuitry of the sensor control circuit is simplified since the timing circuit 32 may control the operations of reference counter 37 and detect counter 34 using the same output signal.

According to the above described sensor control circuit, the liquid body can be reliably detected, while slow changes to the probe oscillator can be filtered out, such as those caused by temperature variations or droplets of liquid or foam adhering to the probe 11.

When probe 11 contacts liquid, the frequency shift of probe oscillator 31 is significant enough to cause timing circuit 32 to decrement reference counter 37 and detect counter 34 for an extended period of time. Thus, detect counter 34 is able to be decrement its count successively (without being reset) until it decrements past a fixed count (the predetermined number) and indicates the presence of the liquid body. Because the downward frequency shift of the probe oscillator 31 is significant when the probe 11 contacts the liquid body, the probe counter 33 outputs a significantly lower count at each regular interval. While timing circuit 32 continues to decrement the reference count in reference counter 37, the reference count will not decrement past the output of the probe counter 37 (at the end of the regular interval) for a significantly long time period. This allows the detect counter 34 to decrement the predetermined number of times without being reset in order to indicate the presence of liquid.

In contrast, when the probe 11 is subject to temperature variations, liquid droplets, or foam, for example, the frequency of probe oscillator 31 also may shift downwards (and thus the probe count of probe counter 33 may be lower at the regular intervals). However, because the frequency shift of the probe oscillator 31 is not as great as when the probe 11 contacts the liquid body, the reference count in reference counter 37 can succeed in decrementing past the probe count (at the regular interval) before the detect counter 34 consecutively decrements the predetermined number of times (to indicate the presence of liquid). Thus, the timing circuit 32 will reset the detect counter 34 at the next reference interval since the reference count in reference counter 37 will be less than the probe count of probe counter 33. Therefore, the predetermined number is never reached in the detect counter 34 and no determination of liquid contact is made.

Figure 4:
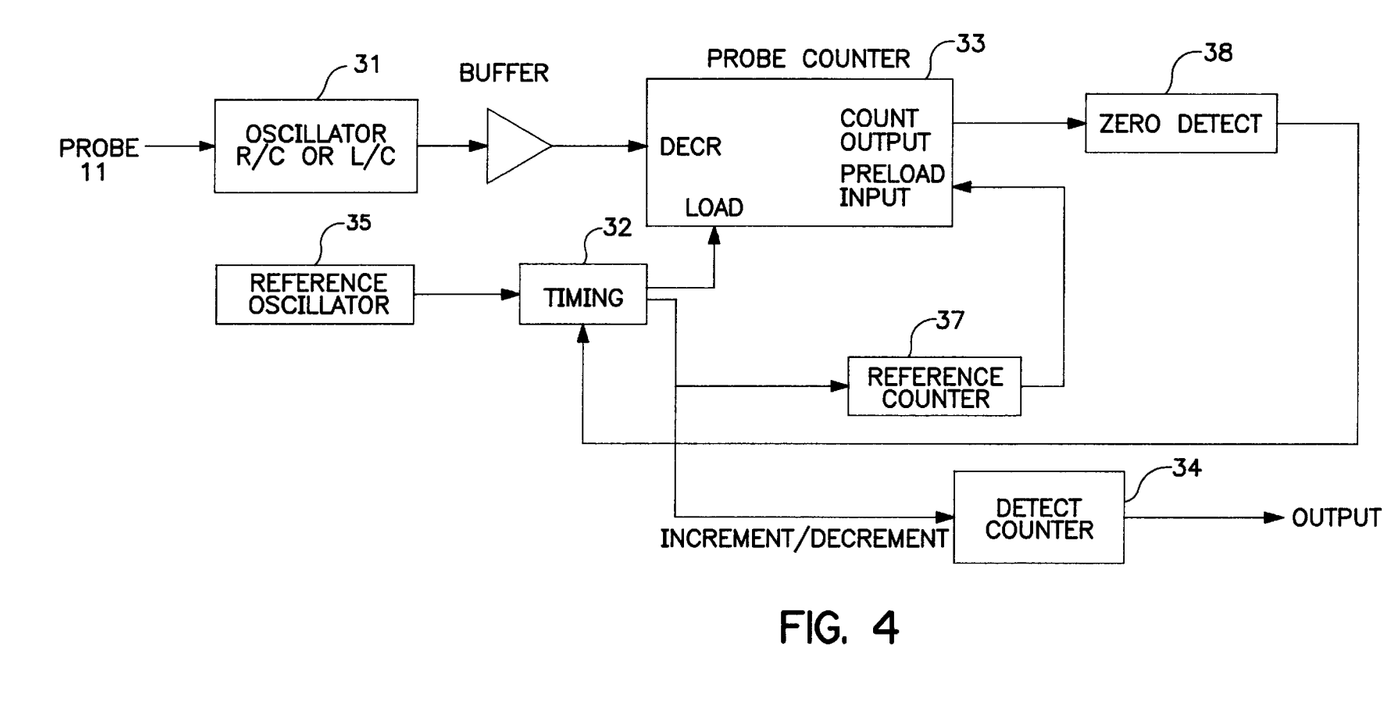

FIG. 4 is a schematic block diagram of another embodiment of liquid level sensor control circuit 30. Illustrated in FIG. 4 are probe 11 and R/C or L/C probe oscillator 31. Also shown are probe counter 33, reference counter 37 and detect counter 34. Timing circuit 32 and reference oscillator 35 are also shown in FIG. 4, along with zero detect 38.

In the liquid level sensor control circuit of FIG. 4, in operation, probe 11 changes the tuning of the R/C or L/C oscillator 31, shifting down the frequency of the signal output by probe oscillator 31, when probe 11 is in contact with a liquid body. Probe counter 33 decrements a probe count for each cycle of the frequency of the signal output by probe oscillator 31.

Zero detect circuit 38 is coupled to the probe counter 33 to receive the probe count of probe counter 33 as an input. When zero detect circuit 38 detects the probe count has reached zero, zero detect circuit 38 outputs a zero detect signal to timing circuit 32.

At regular intervals, timing circuit 32 loads probe counter 33 with a reference count stored in reference counter 37. Because timing circuit 32 loads the reference count into probe counter 33 at every regular interval, receipt of a zero detect signal from zero detect circuit 38 indicates the reference count is smaller than the number of cycles, within the regular interval, of the frequency of the signal output by probe oscillator 31. If the reference count is larger than the number of cycles within the regular interval, no zero detect signal will be output by zero detect circuit 38 since the reference count will be loaded into probe counter 33 before the probe counter 33 is able to be decremented to zero.

In response to the receipt of the zero detect signal from zero detect circuit 38, timing circuit 32 increments the reference count in reference counter 37. If the zero detect signal is not received from zero detect circuit 38, timing circuit 32 decrements the reference count. Thus, the reference count is respectively incremented or decremented to slowly follow the larger or smaller number of cycles per regular interval of the signal output by probe oscillator 31.

Detect counter 34 functions in a similar manner as described above with respect to FIG. 3. Detect counter 34 counts up when reference counter 37 counts down, and resets when reference counter 37 counts up. When detect counter 34 reaches a predetermined number, the output is set, indicating the presence of liquid. In this way, the liquid sensing allows the system to compensate for frequency drift in the probe oscillator, because slow changes are followed without generating a spurious output.

Figure 5:
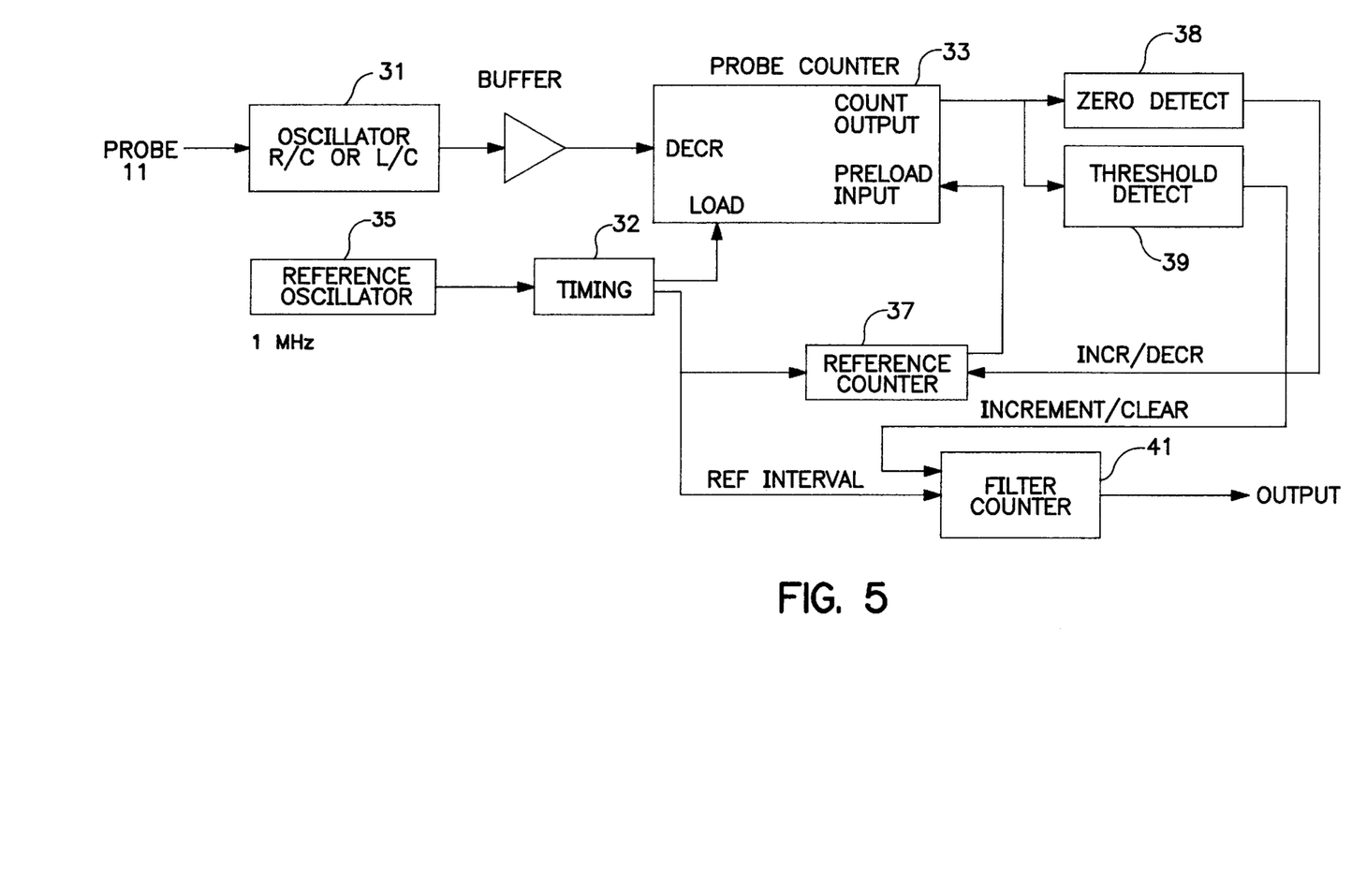

FIG. 5 is a schematic block diagram of a further embodiment of liquid level sensor control circuit 30. Illustrated in FIG. 5 are probe 11 and R/C or L/C probe oscillator 31. Also shown are probe counter 33, reference counter 37 and filter counter 41. Timing circuit 32 and reference oscillator 35 are also shown in FIG. 5, along with zero detect 38 and threshold detect 39.

As in FIG. 4, in FIG. 5 in operation, probe 11 changes the tuning of the R/C or L/C oscillator, shifting the frequency down when in contact with liquid. Probe counter 33 counts down once for each cycle of the frequency of the signal output by probe oscillator 31. At regular intervals, timing circuit 32 loads probe counter 33 with the reference count contained in reference counter 37. If zero detect circuit 38 indicates that the probe count of probe counter 33 has passed through zero sometime during the regular interval, timing circuit 32 increments the reference count of reference counter 37. Otherwise, if no zero detect signal is received, timing circuit 32 decrements the reference count of reference counter 37 at the end of the regular interval.

Further, in relation to FIG. 5, threshold detect circuit 39 receives the probe count of probe counter 33 as an input. Threshold detect circuit 39 outputs a threshold detect signal as an output when threshold detect circuit 39 determines the probe count of probe counter 33 has fallen below a threshold value.

Filter counter 41 is coupled to timing circuit 32 to receive a reference interval signal indicating the end of the reference interval. Also, filter counter 41 is coupled to threshold detect circuit 39 to receive the threshold detect signal. At the end of the reference interval, filter counter 41 counts up if no threshold detect signal has been received (probe counter 33 has not passed through the threshold count). At the end of the reference interval, if a threshold detect signal has been received, filter counter 41 resets. When filter counter 41 reaches a predetermined count, it outputs a liquid detection signal, indicating the presence of a liquid body.

Because this embodiment utilizes both a zero detect circuit to modify the reference count in the reference counter and a threshold detect circuit to increment the filter counter, the liquid sensing system may sense the presence of the liquid body faster and with more accuracy. When the threshold value is greater than zero, the filter counter does not need to count up to as large a predetermined number before indicating the presence of liquid body (as compared to the detect counters in the embodiments illustrated in FIGS. 3 and 4). When threshold detect circuit 41 outputs a threshold detect signal, this indicates reference count in reference counter 37 is close to (within the threshold value) the cycles of oscillator 31 per reference interval. Thus, because no significant change of the frequency of oscillator 31 has occurred, it is determined that no liquid body has been contacted and the filter counter 41 is reset.

On the other hand, when the threshold detect circuit 41 fails to output a threshold detect signal within the reference interval, this indicates the cycles of oscillator 31 per reference interval are less than the reference count by at least the threshold value. This indicates that the frequency of the oscillator 31 has shifted significantly downward, and thus the filter counter is incremented. If this significant shift is a spurious output from the probe, noise, or some other transient error, the sensor system will not indicate the sensing of the liquid body because the threshold detect signal will reset the filter counter 41 when the transient error disappears in a subsequent reference interval. However, if no threshold detect signal is received by the filter counter within the predetermined number of successive reference intervals, it is determined that the liquid body is in contact with the probe 11.

Additionally, this embodiment of liquid sensing allows the system to compensate for frequency drift in the probe oscillator, because slow changes are followed by the reference counter.

The values of the detection, threshold and filter count may be changed to alter the sensitivity and noise immunity of the circuit. A further embodiment of the invention contemplates these values along with the reference interval to be programmable. This allows adaption of the probe system to each individual's needs.

A number of frequencies and timings are conceivable within the scope of the present invention. As one of skilled in the art will recognize, the values utilized in the counters and the operation of the control logic in the timing circuit 32 will depend on many factors, such as the liquid to be sensed, the sensing environment, the sensitivity desired, the speed desired, etc. As one example, the probe oscillator can be set to oscillate at a frequency of from about 5 to 7 MHz, the reference oscillator at 1 MHz, the reference interval being 2 milliseconds (1 MHz/500), and the detection threshold (if using the implementation illustrated in FIG. 5) being between 6 and 12.

In FIGS. 3–5, the counters and timing can all be embedded in a single programmable logic IC. Also, the detection threshold and filter count values can be varied for the size of container and type of liquid being detected. And, as an alternative to hardware implementation, the detection algorithm can be implemented in software.

While there have been described what are presently believed to be the preferred embodiments of the invention, it will be apparent to one skilled in the art that numerous changes can be made in the structure, proportions and conditions set forth in the foregoing embodiments without departing from the invention as described herein and as defined in the appended claims. For example, the embodiments illustrated in FIGS. 3 and 4 may be adapted to incorporate the threshold detect circuit and the filter counter. In addition, other circuitry will be obvious to those skilled in the art to perform the inventive features of this invention other than those described above.

I claim:

1. A liquid sensor for sensing a surface of a liquid, comprising:

a probe for touching the surface of the liquid;

a probe oscillator coupled to the probe, outputting a frequency signal;

a probe counter outputting a cycle count as a function of counted cycles of the frequency signal output by the probe oscillator;

a reference counter storing and outputting a reference count which represents frequency;

a comparator comparing the cycle count output by the probe counter to the reference count output by the reference counter;

a liquid detection counter, maintaining a third count in response to a preliminary detection signal and outputting a detection signal indicating the contact of the probe to the surface of said liquid when said third count passes a first predetermined value; and a controller, outputting at regular intervals, such that
when the comparator indicates the reference count is less than the cycle count, the controller increases the reference count stored in the reference counter and resets the liquid detection counter,
when the comparator indicates the reference count is greater than the cycle count, the controller decreases the reference count stored in the reference counter and outputs the preliminary detection signal to the liquid detection counter, and
resetting the cycle count in the probe counter.

2. The liquid sensor of claim 1,
wherein said controller increases and decreases the reference count by a second predetermined value.

3. The liquid sensor of claim 2, wherein
the first predetermined value, the second predetermined value and the predetermined time period are programmable.

4. The liquid sensor of claim 1,
wherein said controller increments and decrements the reference count by one.

5. The liquid sensor of claim 1,
wherein the controller outputs an increment and decrement signal on an increment/decrement signal line to said reference counter and the liquid detection counter in response to the comparator,
the reference counter respectively increments and decrements the reference counter in response to the increment and decrement signals, and
the liquid detection counter decrements the third count in response to the decrement signal, resets the third count in response to the increment signal and outputs the detection signal when the third count is less than the first predetermined value.

6. The liquid sensor of claim 1, wherein
the liquid detection counter increments the third count in response to the preliminary detection signal and outputs the detection signal when the third count is greater than the first predetermined value.

7. The liquid sensor of claim 1, wherein
the cycle count output by the probe counter equals the number of counted cycles of the frequency signal output by the probe oscillator from the start of a predetermined time period.

8. A liquid sensor for sensing a surface of a liquid, comprising:
a probe for touching the surface of the liquid;
a probe oscillator coupled to the probe, outputting a frequency signal;
a reference counter storing and outputting a reference count which represents frequency;
a probe counter, loading the reference count stored in the reference counter as a second count in response to a load signal, and decrementing the second count as a function of counted cycles of the frequency signal output by the probe oscillator, and outputting the second count;
a zero detect circuit, coupled to the probe counter to receive the second count as an input, and outputting a zero detect signal when the probe count equals or is less than zero;

a third counter, maintaining a third count in response to a preliminary detection signal and outputting a detection signal indicating the contact of the probe to the surface of said liquid when said third count passes a first predetermined value; and a controller, increasing the reference count in the reference counter and resetting the third counter when a zero detect signal is received from the zero detect circuit, decreasing the reference count in the reference counter and outputting the preliminary detection signal to the third counter at regular intervals when no zero detect signal has been received since the previous interval, and outputting the load signal to said second counter at every interval.

9. The liquid sensor of claim 8,
wherein said controller increases and decreases the reference count by a second predetermined value.

10. The liquid sensor of claim 9, wherein
the first predetermined value, the second predetermined value and the predetermined time period are programmable.

11. The liquid sensor of claim 8,
wherein said controller increments and decrements the reference count by one.

12. The liquid sensor of claim 8,
wherein the controller outputs an increment and decrement signal on an increment/decrement signal line to said reference counter and the third counter,
the reference counter respectively increments and decrements the reference counter in response to the increment and decrement signals, and
the third counter decrements the third count in response to the decrement signal, resets the third count in response to the increment signal and outputs the detection signal when the third count is less than the first predetermined value.

13. The liquid sensor of claim 12, wherein
the third counter increments the third count in response to the preliminary detection signal and outputs the detection signal when the third count is greater than the first predetermined value.

14. The liquid sensor of claim 8, wherein
the second count output by the probe counter is decremented by one for every counted cycle of the frequency signal output by the probe oscillator.

15. A liquid sensor for sensing a surface of a liquid, comprising:
a probe for touching the surface of the liquid;
a probe oscillator coupled to the probe, outputting a frequency signal;
a reference counter storing and outputting a reference count which represents frequency;
a probe counter, loading the reference count stored in the reference counter as a second count in response to a load signal, and decrementing the second count as a function of counted cycles of the frequency signal output by the probe oscillator, and outputting the second count;
a zero detect circuit, coupled to the probe counter to receive the second count as an input, and making a zero detection when the probe count equals or is less than zero;
a threshold detect circuit, coupled to the probe counter to receive the second count as an input, and making a threshold detection when the probe count equals or is less than a threshold value; and a controller, increasing the reference count in the reference counter when zero detection is made by the zero detect circuit, decreasing the reference count in the reference counter at regular intervals when no zero detection is made by the zero detect circuit since the previous interval, indicating contact of the probe with the surface if the liquid when no threshold detection is made by the threshold detect circuit since the previous interval, and outputting the load signal to said second counter at every interval.

16. The liquid sensor of claim 15, wherein said controller increases and decreases the reference count by a second predetermined value.

17. The liquid sensor of claim 16, wherein the first predetermined value, the second predetermined value and the predetermined time period are programmable.

18. The liquid sensor of claim 15, wherein said controller increments and decrements the reference count by one.

19. The liquid sensor of claim 15, wherein the second count output by the probe counter is decremented by one for every counted cycle of the frequency signal output by the probe oscillator.

20. The liquid sensor of claim 15, further comprising a third counter maintaining a third count that is incremented when no threshold detection is made, is reset when threshold detection is made, and outputting a detection signal indicating the contact of the probe with the surface of the liquid when said third count passes a first predetermined value.

21. The liquid sensor of claim 20, wherein the controller outputs a reference interval signal to the probe counter, the reference counter and the third counter, the probe counter loads the reference count in the reference counter in response to the reference interval signal from the controller, the reference counter respectively increments or decrements the reference count in response to an increment or decrement signal received from the zero detect circuit when the reference interval signal is received from the controller, and the third counter respectively increments or clears the third count in response to an increment or clear signal from the threshold detect circuit and when the reference interval signal is received from the controller.

22. A method for sensing a surface of a liquid with a probe, comprising:
 (a) generating a frequency signal in response to the location of the probe;
 (b) counting the cycles of the frequency signal and generating a cycle count;
 (c) comparing the cycle count to a reference value;
 (d) at regular intervals,
  (d1) when the reference value is greater than the cycle count, decreasing the reference value and incrementing a detection count,
  (d2) when the reference value is less than the cycle count, increasing the reference value and resetting the detection count to zero, and
  (d3) resetting a cycle count to zero; and
 (e) determining the detection of the liquid surface when the detection count is greater than a predetermined number.

23. A liquid sensor for sensing a surface of a liquid, comprising:

a probe for touching the surface of the liquid;

a probe oscillator coupled to the probe, outputting a frequency signal;

a probe counter outputting a cycle count as a function of counted cycles of the frequency signal output by the probe oscillator;

a reference counter storing and outputting a reference count which represents the frequency;

a comparator comparing the cycle count output by the probe counter to the reference count output by the reference counter; and a controller, outputting at regular intervals, such that,
 when the comparator indicates the reference count is less than the cycle count, the controller increases the reference count stored in the reference counter and resets the liquid detection counter,
 when the comparator indicates the reference count is greater than the cycle count, the controller decreases the reference count stored in the reference counter and outputs the preliminary detection signal to the liquid detection counter, and resets the cycle count in the probe counter;
when the difference between the reference count and the cycle count is more than a predetermined amount, said difference indicates a sufficiently large frequency shift to thereby indicate contact of the probe with the surface of the liquid.

* * * * *